United States Patent [19]

Crossley et al.

[11] 4,349,555
[45] Sep. 14, 1982

[54] DITHIOCOMPOUNDS

[75] Inventors: Roger Crossley, Reading; David G. Hill, Cookham, both of England

[73] Assignee: John Wyeth & Brother Limited, Maidenhead, England

[21] Appl. No.: 98,419

[22] Filed: Nov. 29, 1979

[30] Foreign Application Priority Data

Nov. 30, 1978 [GB] United Kingdom ............... 46723/78

[51] Int. Cl.$^3$ ................. A61K 31/415; A61K 31/425; A61K 31/44; C07D 498/00
[52] U.S. Cl. .................................... 424/263; 546/275; 546/278; 546/290
[58] Field of Search ....................... 546/275, 278, 290; 424/263

[56] References Cited

U.S. PATENT DOCUMENTS 4,177,350 12/1979 Zirngibl et al. ..................... 546/278

FOREIGN PATENT DOCUMENTS 992157 5/1965 United Kingdom ................ 546/290

OTHER PUBLICATIONS

Renault et al., Chim. Ther., 1966, pp. 337–338.
Burger, Medicinal Chemistry, 2nd Ed., pp. 79–81, Interscience Pub. Co., NY (1960).
Renault et al., Chem. Abstracts, vol. 66, Abst. No. 55349p (1967) (abstract of R supra).

Primary Examiner—John D. Randolph
Attorney, Agent, or Firm—George Tarnowski

[57] ABSTRACT

Novel compounds of formula I are described wherein R is lower alkyl, phenyl or aralkyl of 7 to 12 carbon atoms, $R^1$ is hydrogen, lower alkyl, hydroxyloweralkyl, loweralkoxyloweralkyl, lower alkoxy, halogen, formyl, phenyl, phenylalkyl or acetal [$CH(OR^2)_2$ where $R^2$ is lower alkyl, or two $R^4$ radicals are joined to form a lower alkylene chain], m is 1 or 2, Z is an anion, A is an alkylene radical having from 1 to 3 carbon atoms, which may be substituted by lower alkyl of 1 to 6 carbon atoms, S is sulphur and X is a benzothiazole, benzimidazole, benzoxazole, or phenyl radical which may be substituted and acid addition or quaternary ammonium salts of compounds wherein X is a benzimidazole radical. The compounds are used for the treatment of ulcers or hypersecretion. Treatment methods are claimed as well as pharmaceutical compositions.

18 Claims, No Drawings

DITHIOCOMPOUNDS

The invention relates to novel heterocyclic compounds which exhibit anti-ulcer and/or anti-secretory activity.

During the course of our searches for novel anti-ulcer agents we have made a new class of dithio compounds which contain a pyridinium radical. The compounds which we have prepared possess anti-ulcer and/or anti-secretory activity.

Accordingly the invention provides a compound of formula

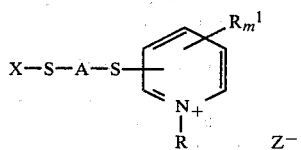

wherein R is lower alkyl, phenyl or aralkyl of 7 to 12 carbon atoms, $R^1$ is hydrogen, lower alkyl, hydroxyloweralkyl, loweralkoxyloweralkyl, lower alkoxy, halogen, formyl, phenyl, phenylalkyl or acetal [$CH(OR^2)_2$ where $R^2$ is lower alkyl, or two $R^4$ radicals are joined to form a lower alkylene chain], m is 1 or 2, Z is an anion, A is an alkylene radical having from 1 to 3 carbon atoms, which may be substituted by lower alkyl of 1 to 6 carbon atoms, S is sulphur and X is a benzothiazole, benzimidazole, benzoxazole, or phenyl radical which may be substituted by one or more of the following radicals; halogen, nitro, lower alkoxy, aralkoxy of 7 to 12 carbon atoms, hydroxy, hydroxyloweralkyl, loweralkoxyloweralkyl, amino, lower alkylamino, diloweralkylamino, trifluoromethyl, lower alkyl, aryl or aralkyl of 7 to 12 carbon atoms or disubstituted by a loweralkylenedioxy radical and acid addition or quaternary ammonium salts of compounds wherein X is a benzimidazole radical.

X is preferably a phenyl or substituted phenyl radical, for example, substituted by one or two of the substituents identified above, eg halogen such as chlorine, bromine, fluorine or iodine.

The radical A is preferably a methylene or ethylene radical.

$Z^-$ may be a halide ion, or an organic sulphonate ion such as arylsulphonate, eg p-toluene sulphonate, lower alkylsulphonate, eg methylsulphonate, or aralkylsulphonate.

In this specification the term lower alkyl means an alkyl radical of 1 to 6 carbon atoms e.g. methyl, ethyl, n-propyl, isopropyl, n-butyl, s-butyl, t-butyl, n-pentyl and n-hexyl. A lower alkoxy substituent is an alkoxy radical in which the alkyl portion is as defined for a lower alkyl radical. Whenever the term lower alkyl is used as part of another radical e.g. arylloweralkyl, the lower alkyl portion has 1 to 6 carbon atoms. The aralkyl radical of 7 to 12 carbon atoms is preferably phenyl lower alkyl.

The acid addition salts of compounds of formula I may be of an organic or inorganic acid e.g. hydrochloric, hydrobromic, phosphoric, sulphuric, nitric, citric, acetic, formic, fumaric, maleic, tartaric, embonic, methane sulphonic and p-toluene sulphonic acids.

Compounds of formula I were tested for anti-ulcer activity by the stress-induced erosion test of Senay & Levine, Proc. Soc. Exp. Biol. Med., 124, 1221-3 (1967) and anti-secretory activity by the test of H. Shay, D. Sun and H. Greenstein, Gastroenterology, 1954, 26,903-13 as exemplified by Doreen Beattie et al J. Med. Chem. 20, 714 (1977). Compounds which possess one or both activities in these tests are considered to be anti-ulcer agents which can be used for the treatment of ulcers or hyper-secretion in mammals.

In a further aspect the invention provides a pharmaceutical composition comprising a compound of formula I or a salt thereof as defined above and a pharmaceutically acceptable carrier.

For the pharmaceutical carrier any suitable carrier known in the art can be used to prepare the pharmaceutical compositions. In such a composition, the carrier may be a solid, liquid, or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more e.g. 25 mg to 250 mg, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

The invention also includes a method of preparing a compound of formula I or a salt thereof as defined above which method comprises reacting (A) a compound of formula II X—S—A—Hal    II wherein X, S and A are as defined above and Hal is a halogen atom, such as chlorine, bromine or iodine, with a pyridothione of formula III or a thiol of formula IIIA

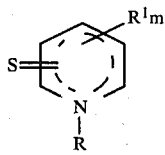

III

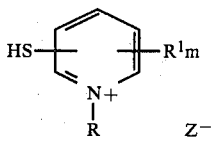

IIIA wherein R, R¹, m and Z are as defined above and two double bonds are present in the heterocyclic ring of formula III, or (B) a compound of formula IV

X—SH    IV wherein X is as defined above, with a compound of formula

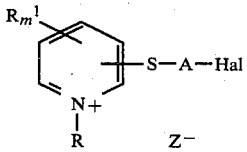

V wherein R, R¹, m Z⁻, S, A and Hal are as defined in A above and if desired converting the product to an acid addition or quaternary ammonium salt as defined above, when X is a benzimidazole radical, or (C) a compound of formula VI

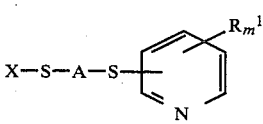

wherein X,S,A,R¹ and m are as defined above may be reacted with an alkylating, arylating or aralkylating agent containing the groups R and Z, eg a lower alkyl-, or aralkylhalide or a loweralkyl-, aryl or aralkylsulphonic acid lower alkyl or aralkyl ester.

A compound I in which Z⁻ is one particular anion may be converted to another in which Z⁻ is a different anion by anion exchange, eg chloride may be exchanged for iodide by reaction of a chloride of formula I with sodium iodide in ethanol or other suitable solvent.

The invention includes a method of treating ulcers or hypersecretion in a mammal which method comprises administering to said mammal an effective amount of an anti-ulcer agent of formula I, or a salt thereof, as defined above. The amount used will depend on the needs of the mammal being treated and the activity of the compound used but may vary from 1 to 100 mg/kg.

The following examples illustrate the invention:

EXAMPLE 1

2-((2-Benzothiazolylthio)methyl)thio)-1-methyl pyridinium chloride

A mixture of 2-chloromethylthiobenzothiazole (2.15 g) and 1-methyl-2-pyridothione (1.25 g) in ethanol (7 ml) was refluxed for 5 hours. The solvent was removed in vacuo and the residue triturated with acetone to give the title compound as a quarter hydrate, (2.2 g) mp. 132°–5° C.

(Found: C, 48.5; H, 4.0; N, 7.9 $C_{14}H_{13}ClN_2S_3 \cdot \frac{1}{4}H_2O$ requires C, 48.7; H, 3.9; N, 8.1%).

EXAMPLE 2

2-((((4-Chlorophenyl)thio)methyl)thio)-1-methyl-pyridinium chloride

Chloromethyl 4-chlorophenyl sulphide (1.93 g) and 1-methyl-2-pyridothione (1.25 g) in ethanol (10 ml) were heated at reflux for 4 hours. The solvent was removed by evaporation and the residue was triturated at length with ether and with acetone to give a solid which was removed by filtration and dried to give the title compound (1.5 g) mp 159°–60° C.

(Found: C, 48.9; H, 4.3; N, 4.4. $C_{13}H_{13}Cl_2NS_2$ requires C, 49.1; H, 4.1; N, 4.4%).

EXAMPLE 3

2-(((Phenylthio)methyl)thio)-1-methylpyridinium chloride

Chloromethyl phenyl thioether (90%, 1.76 g) and 1-methyl-2-pyridothione (1.25 g) in ethanol (10 ml) were heated at reflux for 4 hours. The solvent was evaporated and the residue was triturated with ether and with acetone to give the title compound as a three quarter hydrate (1.4 g) mp. 138°–41° C.

(Found: C, 52.8; H, 5.0; N, 4.75. $C_{13}H_{14}ClNS_2 \cdot \frac{3}{4}H_2O$ requires C, 52.5; H, 5.25; N, 4.7%).

EXAMPLE 4

2-(((2-Benzimidazolylthio)methyl)thio)-1-methyl-pyridinium chloride

By the method of example 1, reaction of 2-chloromethylthiobenzimidazole and 1-methyl-2-pyridothione gives the title compound.

EXAMPLE 5

2-(((2-Benzoxazolylethio)methyl)thio)-1-methyl-pyridinium chloride

By the method described in example 1, reaction of 2-chloromethylbenzoxazole and 1-methyl-2-pyridothione gives the title compound.

EXAMPLE 6

2-(((4-Methylphenylthio)methyl)thio)-1-methyl-pyridinium chloride

Chloromethyl 4-methylphenyl sulphide and 1-methyl-2-pyridothione are reacted together by the method of example 2 to give the title compound.

EXAMPLE 7

By the method described in example 2 the following starting materials are reacted with 1-methyl-2-pyridothione to give the following products:

| Starting Material | Product |
|---|---|
| (a) Chloromethyl 4-methoxyphenyl sulphide | 2-(((4-Methoxyphenylthio)methyl)thio)-1-methyl pyridinium chloride. |
| (b) Chloromethyl 2,5-dichlorophenyl sulphide | 2-(((2,5-dichlorophenyl-thio)methyl)thio)-1-methyl-pyridinium chloride |
| (c) Chloromethyl 4-bromophenyl sulphide | 2-(((4-bromophenylthio)methyl)thio)-1-methyl-pyridinium chloride. |
| (d) Bromomethyl phenyl sulphide | 2-(((phenylthio)methyl)thio)-1-methylpyridinium bromide |

EXAMPLE 8

By the method described in example 2 the following starting materials are reacted with chloromethyl phenyl sulphide to give the following products:

| Starting Material | Product |
|---|---|
| (a) 1-ethyl-2-pyridothione | 2-(((Phenylthio)methyl)thio)-1-ethylpyridinium chloride. |
| (b) 1-n-butyl-2-pyridothione | 2-(((Phenylthio)methyl)thio)-1-(1-n-butyl) pyridinium chloride. |
| (c) 1-benzyl-2-pyridothione | 2-(((Phenylthio)methyl)thio)-1-benzylpyridinium chloride. |

EXAMPLE 9

2((Phenylthio)methyl)thio)-3-(diethoxy)methyl-1-phenylpyridinium chloride

A mixture of chloromethyl phenyl thioether and 3-formyl-1-phenyl-2-pyridothione is heated in ethanol following the procedure of example 3 to obtain the title compound.

EXAMPLE 10

2-(((Phenylthio)methyl)thio)-3-formyl-1-methyl-pyridinium bromide

A mixture of bromomethyl phenyl thioether and 3-formyl-1-methyl-2-pyridothione is heated in acetonitrile following the procedure of example 3 to obtain the title compound.

EXAMPLE 11

2-(((Phenylthio)methyl)thio)-3-hydroxymethyl-1-phenylpyridinium bromide

Bromomethylphenylthioether and 3-hydroxymethyl-1-phenyl-2-pyridothione are heated under reflux in acetonitrile to obtain the title compound.

| | Pharmacological Test Results | | | |
|---|---|---|---|---|
| | Stress induced erosion (Senay & Levine) | | Anti-secretory (Shay et al) | |
| Compound [Product of Example No.] | Dose mg/kg | % Inhibition | Dose mg/kg | % change in vol |
| 1 | 100 | 81 | 30 | −40 |
| 2 | 100 | 60 | 30 | −54 |
| | 30 | 69 | | |
| 3 | 100 | — | 30 | −71 |

Pharmaceutical Compositions

The following examples illustrate the preparation of unit dosage form of pharmaceutical compositions according to the invention.

EXAMPLE A

| Antacid Tablet (chewable) | |
|---|---|
| Saccharin | 1.0 mg. |
| Hydrated alumina sucrose powder | 750.0 mg. |
| 2-(((Benzothiazolylthio)methyl)thio)-1-methylpyridinium chloride | 100.0 mg. |
| Mannitol B.P. | 170.0 mg. |
| Maize starch B.P. dried | 30.0 mg. |
| Talc. purified B.P. | 28.0 mg. |
| Magnesium stearate B.P. | 20.0 mg. |
| Peppermint oil B.P. | 1.0 mg. |
| | 1100.0 mg. |

Antacid tablets of the above formulation are prepared by the following procedure. Triturate peppermint oil with talc (screen 40 mesh). Add the triturate, and other ingredients to a blender and mix thoroughly. Slug the powder to large hard slugs. Granulate the slugs through a 14 mesh screen. Compress the granules on a suitable compression machine to give tablets of the required size.

EXAMPLE B

| Anti-ulcer tablet (without antacid) | mg/tablet |
|---|---|
| 2-(((4-Chlorophenyl)thio)methyl)thio-1-methylpyridinium chloride | 100 mg. |
| Celutab | 147.5 mg. |
| Mg. Stearate | 2.5 mg. |
| | 250.0 mg. |

The tablets are prepared by the following method. Blend the ingredients in a suitable blender. Compress the blended ingredients on a suitable compression machine to form tablets of the above composition. Celutab is a commercial product comprising 90-2% dextrose, 3-5% maltose, the remainder being higher glucose saccharides. The product is spray crystallised.

EXAMPLE C

Example B was repeated replacing the active ingredient by 100 mg. of 2-(((Phenylthio)methyl)thio)-1-methylpyridinium chloride.

We claim:

1. A compound of formula

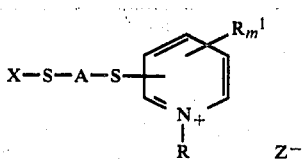

wherein R is lower alkyl, phenyl or aralkyl of 7 to 12 carbon atoms, $R^1$ is hydrogen, lower alkyl, hydroxyloweralkyl, loweralkoxyloweralkyl, lower alkoxy, halogen, formyl, phenyl, phenylalkyl or acetal [$CH(OR^2)_2$ where $R^2$ is lower alkyl, or two $R^4$ radicals are joined to form a lower alkylene chain], m is 1 or 2, Z is an anion, A is an alkylene radical having from 1 to 3 carbon atoms, which may be substituted by lower alkyl of 1 to 6 carbon atoms, S is sulphur and X is a benzothiazole, benzimidazole, benzoxazole, or phenyl radical which may be substituted by one or more of the following radicals; halogen, nitro, lower alkoxy, aralkoxy of 7 to 12 carbon atoms, hydroxy, hydroxyloweralkyl, loweralkoxyloweralkyl, amino, lower alkylamino, diloweralkylamino, trifluoromethyl, lower alkyl, aryl or aralkyl of 7 to 12 carbon atoms or disubstituted by a loweralkylenedioxy radical and acid addition or quaternary ammonium salts of compounds wherein X is a benzimidazole radical.

2. A compound as claimed in claim 1, wherein A is methylene.

3. A compound as claimed in claim 1, wherein R is methyl.

4. A compound as claimed in claim 1, wherein X is phenyl or halophenyl.

5. A compound as claimed in claim 1, which is a 2-((2-benzothiazolylthio)methyl)thio)-1-methyl pyridinium halide.

6. A compound as claimed in claim 1, which is 2-((2-benzothiazolylthio)methyl)thio)-1-methyl pyridinium chloride.

7. A compound as claimed in claim 1, which is a 2-((((-4-chlorophenyl)thio)methyl)thio)-1-methylpyridinium halide.

8. A compound as claimed in claim 1, which is 2-((((-4-chlorophenyl)thio)methyl)thio)-1-methylpyridinium chloride.

9. A compound as claimed in claim 1, which is a 2-(((phenylthio)methyl)thio)-1-methylpyridinium halide.

10. A compound as claimed in claim 1, which is 2-(((phenylthio)methyl)thio)-1-methylpyridinium chloride.

11. A method for treating ulcers or hypersecretion in a mammal which comprises administering to said mammal an effective amount of a compound as claimed in claim 1.

12. A method as claimed in claim 11, wherein the compound administered is a 2-((2-benzothiazolylthio)methyl)thio-1-methyl pyridinium halide.

13. A method as claimed in claim 11, wherein the compound administered is a 2-((2-benzothiazolylthio)methyl)thio)-1-methyl pyridinium halide.

14. A method as claimed in claim 11, wherein the compound administered in a 2-((((-4-chlorophenyl)thio)methyl)thio-1-methylpyridinium halide.

15. A pharmaceutical composition for the treatment of ulcers or hypersecretion comprising a compound as claimed in claim 1, and a pharmaceutically acceptable carrier.

16. A pharmaceutical composition as claimed in claim 15 in unit dosage form which comprises from 10 to 500 mg of the compound of formula I per unit dose.

17. A pharmaceutical composition as claimed in claim 15, which also includes an antacid ingredient.

18. A compound of formula

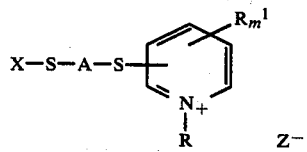

wherein R is lower alkyl, phenyl or aralkyl of 7 to 12 carbon atoms, $R^1$ is hydrogen, lower alkyl, hydroxyloweralkyl, loweralkoxyloweralkyl, lower alkoxy, halogen, formyl, phenyl, phenylalkyl or acetal [$CH(OR^2)_2$ where $R^2$ is lower alkyl, or two $R^4$ radicals are joined to form a lower alkylene chain], m is 1 or 2, Z is an anion, A is an alkylene radical having from 1 to 3 carbon atoms, which may be substituted by lower alkyl of 1 to 6 carbon atoms, S is sulphur and X is a phenyl radical which may be substituted by one or more of the following radicals; halogen, nitro, lower alkoxy, aralkoxy of 7 to 12 carbon atoms, hydroxy, hydroxyloweralkyl, loweralkoxyloweralkyl, amino, loweralkylamino, diloweralkylamino, trifluoromethyl, lower alkyl, aryl or aralkyl of 7 to 12 carbon atoms or disubstituted by a loweralkylenedioxy radical.

* * * * *